United States Patent
Zhe et al.

(10) Patent No.: US 9,814,607 B2
(45) Date of Patent: Nov. 14, 2017

(54) LOW-POWER METHOD AND DEVICE FOR COOLING PROSTHETIC LIMB SOCKET BASED ON PHASE CHANGE

(71) Applicants: Jiang Zhe, Copley, OH (US); Yu Han, Akron, OH (US); THE UNIVERSITY OF AKRON, Akron, OH (US)

(72) Inventors: Jiang Zhe, Copley, OH (US); Yu Han, Akron, OH (US)

(73) Assignee: The University of Akron, Akron, OH (US)

( * ) Notice: Subject to any disclaimer, the term of this patent is extended or adjusted under 35 U.S.C. 154(b) by 8 days.

(21) Appl. No.: 14/889,162

(22) PCT Filed: May 7, 2014

(86) PCT No.: PCT/US2014/037071
§ 371 (c)(1),
(2) Date: Nov. 5, 2015

(87) PCT Pub. No.: WO2014/182767
PCT Pub. Date: Nov. 13, 2014

(65) Prior Publication Data
US 2016/0081822 A1    Mar. 24, 2016

Related U.S. Application Data

(60) Provisional application No. 61/820,233, filed on May 7, 2013.

(51) Int. Cl.
*A61F 2/80* (2006.01)
*A61F 7/10* (2006.01)
(Continued)

(52) U.S. Cl.
CPC .............. *A61F 2/80* (2013.01); *A61F 7/10* (2013.01); *A61F 2002/501* (2013.01);
(Continued)

(58) Field of Classification Search
CPC ........................ A61F 2/80; A61F 2007/0051
See application file for complete search history.

(56) References Cited

U.S. PATENT DOCUMENTS 6,123,716 A    9/2000  Augustine et al.
6,772,825 B2   8/2004  Lachenbruch et al.
(Continued)

FOREIGN PATENT DOCUMENTS

DE    102009056074 A1   11/2009

*Primary Examiner* — Bruce E Snow
(74) *Attorney, Agent, or Firm* — Renner Kenner Greive Bobak Taylor & Weber (57) ABSTRACT

A prosthesis includes a socket for receiving a residual limb, the socket having a socket wall defining a limb-receiving surface; a heat pipe including a working fluid and a wicking structure, the heat pipe having a socket section and a heat sink section, the heat pipe extending along its length through the socket wall proximate to or exposed at the limb-receiving surface, wherein the working fluid has a boiling point of from about 0° C. to 90° C. such that the working fluid is adapted to evaporate to form vapor under the influence of the heat of a residual limb in the socket thus drawing heat from and cooling the residual limb. A heat sink section of the heat pipe passes through the heat sink, the heat sink reducing the temperature of the working fluid.

5 Claims, 8 Drawing Sheets

(51) Int. Cl.
    *A61F 2/50*     (2006.01)
    *A61F 2/74*     (2006.01)
    *A61F 2/76*     (2006.01)
    *A61F 7/00*     (2006.01)

(52) U.S. Cl.
    CPC ... *A61F 2002/74* (2013.01); *A61F 2002/7665* (2013.01); *A61F 2007/0051* (2013.01); *A61F 2007/0058* (2013.01); *A61F 2007/0086* (2013.01); *A61F 2007/105* (2013.01); *A61F 2007/108* (2013.01)

(56) References Cited

U.S. PATENT DOCUMENTS

| | | |
|---|---|---|
| 6,974,484 B2 | 12/2005 | Caspers |
| 2007/0055383 A1 | 3/2007 | King |
| 2009/0228082 A1 | 9/2009 | Ross et al. |
| 2010/0274364 A1 | 10/2010 | Pacanowsky et al. |
| 2011/0306834 A1 | 12/2011 | Schrader et al. |
| 2013/0274896 A1 | 10/2013 | Wang et al. |
| 2014/0025183 A1 | 1/2014 | Kelley et al. |
| 2015/0238330 A1* | 8/2015 | Jonsson ............... A61F 2/80 623/36 |
| 2016/0296350 A1* | 10/2016 | King ................... A61F 2/80 |

* cited by examiner

LOW-POWER METHOD AND DEVICE FOR COOLING PROSTHETIC LIMB SOCKET BASED ON PHASE CHANGE

CROSS-REFERENCE TO RELATED APPLICATIONS

The present application claims priority to U.S. Provisional Patent Application Ser. No. 61/820,233, filed May 7, 2013, the entirety of which is incorporated herein by reference.

BACKGROUND OF THE INVENTION

Heat transfer from a residual limb through a prosthetic device and to the exterior environment is currently limited by poor thermal conductivity of the prosthesis's liner and socket material. The closed environment of the socket of a prosthesis also prevents heat transfer through evaporation (sweating), thereby increasing skin temperature that may cause skin blisters and irritation. Many amputees report that heat and perspiration within a prosthetic socket provide significant discomfort, and the art has moved to provide certain prosthesis cooling systems.

Maintaining a normal temperature at the skin-prosthesis interface under various activities (thermal loads) is a fundamental design requirement for a prosthesis cooling system. The thermal environment inside a prosthesis is affected by heat generation of the limb (thermal load), thermal resistance of the prosthesis and ambient temperature. Hence it remains a challenge to maintain a comfortable socket temperature in various environments while performing different activities.

The prior art provides both air cooling and liquid cooling systems for personal thermoregulation. Air cooling systems based on forced convection remove metabolic heat by fan driven airflow. Due to limited contact area and low heat capacity of air, heat transfer is ineffective and therefore the cooling capacity is insufficient to remove additional heat. Instead, liquid cooling has found a wide range of applications for personal cooling in space, deep ocean, firefighting and other hazardous environments. This type of cooling system has a high coefficient of convective heat transfer which reduces the thermal resistance between a liner and the environment. Additionally, it has an easily adjustable cooling capacity controlled by the liquid's flow rate. However, comfortably using a liquid cooling system requires small diameter tubing, which translates to high power consumption for liquid circulation. Due to the relatively bulky and power intensive equipment needed for this type of liquid cooling system, a tradeoff has to be made between functionality and comfortableness.

Recently, personal cooling systems have been developed that are lightweight, compact and power efficient. Phase change materials (PCM) are a great heat storage media that can be integrated into garments where they absorb excess metabolic heat. However, controlling the cooling rate over various thermal loads remains a difficulty for PCM systems. Thermoelectric device based cooling offers better temperature control with a compact size by varying input electrical power. While it does not have any moving parts, the efficiency of currently available thermoelectric cooling devices is only between 10-15% of Carnot cycles (COP approximately 0.4-1.5). An energy-efficient cooling device is highly desired for a prosthesis cooling that can 1) maintain a constant skin temperature under all range of the thermal loads, 2) be compact and lightweight, 3) be quiet and easy to maintain.

SUMMARY OF THE INVENTION

The present invention provides a residual limb-prosthesis to regulate temperature on the inner surface of a prosthetic socket. The cooling device uses an adjustable thermal resistance to adapt to various activity patterns and environments in a short settling time. To make the device efficient and portable, heat pipes are used to concentrate heat flux from the residual limb into a compact heat sink, where heat is removed by a compact fan/air duct.

In a first embodiment, the present invention provides a residual limb-prosthesis having a socket for receiving a residual limb, a socket having a socket wall defining a limb-receiving surface and a heat pipe. The heat pipe includes a working fluid and a wicking structure, where the heat pipe includes a socket section and a heat sink section. The heat pipe extends along its length through the socket wall which is proximate to or exposed at the limb-receiving surface. The working fluid has a boiling point of from 0° C. or more to 90° C. or less such that the working fluid is adapted to evaporate to form vapor under the influence of the heat of the residual limb in the socket, thus drawing heat from and cooling the residual limb. The present invention further provides a heat sink. The heat sink section of a heat pipe passes through the heat sink, which reduces the temperature of the working fluid so as to condense vapor within the heat pipe back to working fluid. The wicking structure collects the working fluid and draws it back to the socket section.

In a second embodiment, the present invention provides a residual limb-prosthesis as in the first embodiment, wherein the prosthesis comprises a control system for controlling the operation of a heat sink.

In a third embodiment, the present invention provides a residual limb-prosthesis as in the first or second embodiments, wherein the control system includes a heat sensor for monitoring temperature at an interface between a residual limb and the socket, further communicating with a regulator which regulates the effectiveness of the heat sink.

In a fourth embodiment, the present invention provides a residual limb-prosthesis as in any of the first through third embodiments, wherein the control system includes a processor that receives input from the heat sensor and automatically adjusts the regulator to regulate the temperature at the socket surface.

In a fifth embodiment, the present invention provides a residual limb-prosthesis as in any of the first through fourth embodiments, wherein the control system includes a manual control which communicates with a regulator to regulate the effectiveness of the heat sink, thereby adjusting the temperature at the socket surface.

In a sixth embodiment, the present invention provides a residual limb-prosthesis as in any of the first through fifth embodiments, wherein the working fluid is held in a heat pipe under a vacuum such that the boiling point of the working fluid is affected to be different from its normal atmospheric conditions.

In a seventh embodiment, the present invention provides a residual limb-prosthesis as in any of the first through sixth embodiments, wherein the working fluid is selected from water, ethanol, methanol and ammonia and mixtures thereof.

In an eighth embodiment, the present invention provides a residual limb-prosthesis as in any of the first through seventh embodiments, wherein the working fluid is water and is held under a vacuum of 0.6 kPa to 70.2 kPa to provide a boiling point of 0° C. to 90° C.

In a ninth embodiment, the present invention provides a residual limb-prosthesis as in any of the first through eighth embodiments, wherein the residual limb-prosthesis further comprises a liner positioned between a limb in the socket and a heat pipe.

In a tenth embodiment, the present invention provides a residual limb-prosthesis as in any of the first through ninth embodiments, wherein a heat pipe is exposed at the limb-receiving surface so as to come in direct contact with the limb in the socket.

In an eleventh embodiment, the present invention provides a residual limb-prosthesis as in any of the first through tenth embodiments, wherein the heat pipe has a rectangular cross-section relative to the length of the heat pipe. The rectangular cross-section has a height to width ratio of from width ratio of from 1:1 to 5:1. The height of the heat pipe is arranged to face the limb in the socket which increases the surface are of the heat pipe facing a limb in the socket.

In a twelfth embodiment, the present invention provides a residual limb-prosthesis as in any of the first through eleventh embodiments, wherein the heat pipe has a thermal resistance of from 0.16° C./W or more to 0.016° C./W or less.

In a thirteenth embodiment, the present invention provides a residual limb-prosthesis as in any of the first through twelfth embodiments, wherein the heat sink includes a fan operable to blow air across the heat pipe.

In a fourteenth embodiment, the present invention provides a residual limb-prosthesis as in any of the first through thirteenth embodiments, wherein the heat sink includes a plurality of fins that are in direct contact with the heat pipe and a fan blows air across the fins.

In a fifteenth embodiment, the present invention provides a residual limb-prosthesis as in any of the first through fourteenth embodiments, wherein the heat sink includes a cooling package that is filled with a cold source material having a temperature less than that of the vapor formed in the heat pipe.

In a sixteenth embodiment, the present invention provides a residual limb-prosthesis as in any of the first through fifteenth embodiments, wherein the cold source material is selected from ice, dry ice and refrigerant gel.

In a seventeenth embodiment, the present invention provides a residual limb-prosthesis as in any of the first through sixteenth embodiments, wherein the heat sink includes a variable insulator positioned between a cooling package and the heat pipe, which is operable to vary the amount of heat transfer between the heat pipe and the cooling package.

In a eighteenth embodiment, the present invention provides a residual limb-prosthesis as in any of the first through seventeenth embodiments, wherein the heat sink further comprises a heat collector structure which communicates between the heat pipe and the variable insulator.

In a nineteenth embodiment, the present invention provides a residual limb-prosthesis as in any of the first through eighteenth embodiments, wherein the variable insulator includes a heat transfer plate that communicates with the heat collector structure.

In a twentieth embodiment, the present invention provides a residual limb-prosthesis as in any of the first through nineteenth embodiments, wherein the variable insulator includes a second heat transfer plate that communicates with the cooling package.

In a twenty-first embodiment, the present invention provides a residual limb-prosthesis as in any of the first through twentieth embodiments, wherein the variable insulator includes a plurality of chambers that communicate between the heat transfer plate and a second heat transfer plate. The plurality of chambers is adapted to hold air or a coolant such that the insulation offered by the variable insulator is varied by adjustment of the amount of air and coolant in the plurality of chambers.

In a twenty-second embodiment, the present invention provides a residual limb-prosthesis as in any of the first through twenty-first embodiments, wherein the variable insulator includes a coolant chamber that holds the coolant and communicates between the heat transfer plate and the second heat transfer plate. The volume of the coolant in the chamber is varied such that the insulation offered by the variable insulator is varied by adjustment of the volume of the chamber.

In a twenty-third embodiment, the present invention provides a residual limb-prosthesis as in any of the first through twenty-second embodiments, wherein the variable insulator includes heat transfer tubes that communicate with the heat collector structure and a chamber which holds the coolant. The surface are of the contact between the heat transfer tubes and the coolant is variable such that the insulation offered by the variable insulator is varied by adjusting the surface area of contact between the heat transfer tubes and the coolant.

DETAILED DESCRIPTION OF ILLUSTRATIVE EMBODIMENTS

Figure 1:
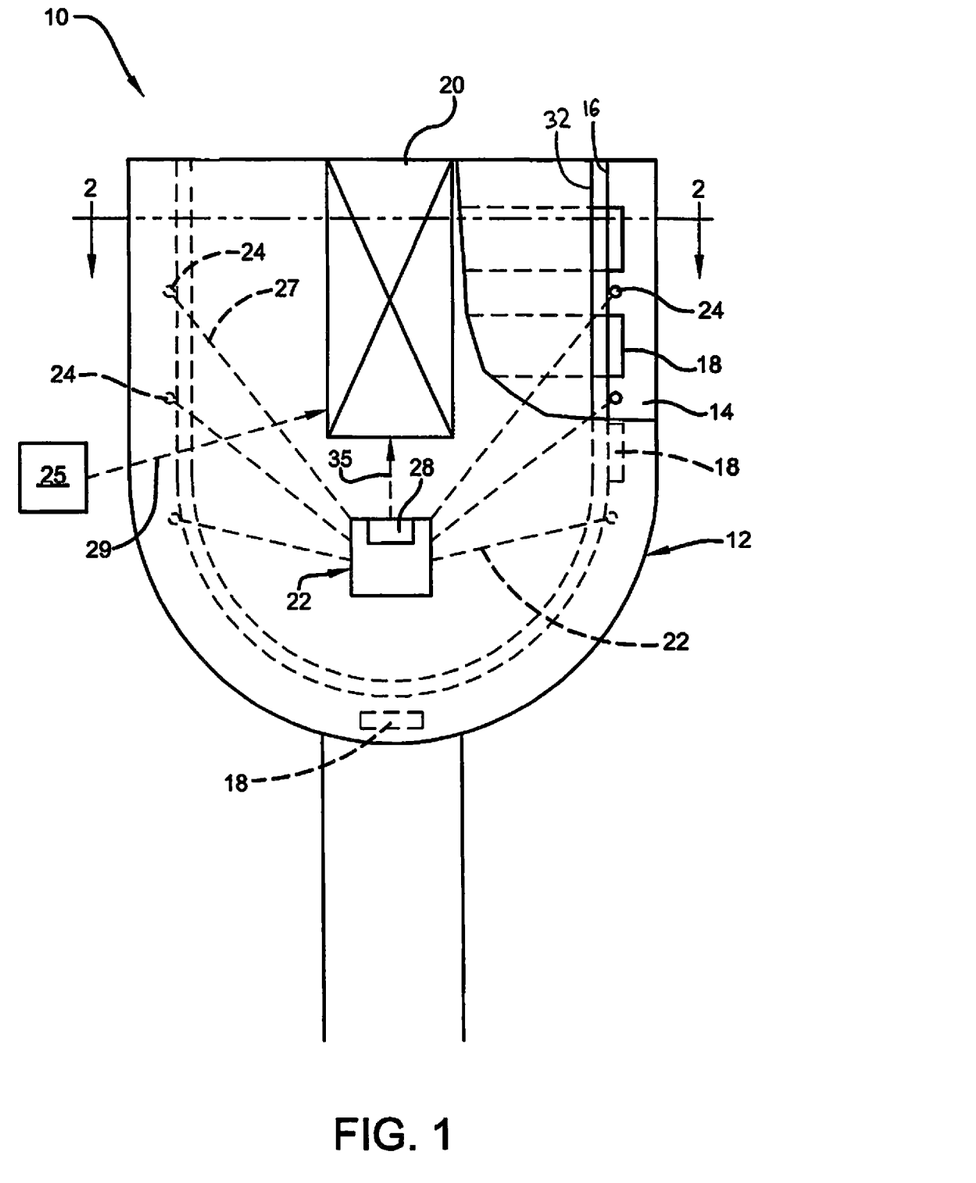
FIG. 1 is a side elevational view of the residual limb-prosthesis in accordance with the present invention.
Figure 2:
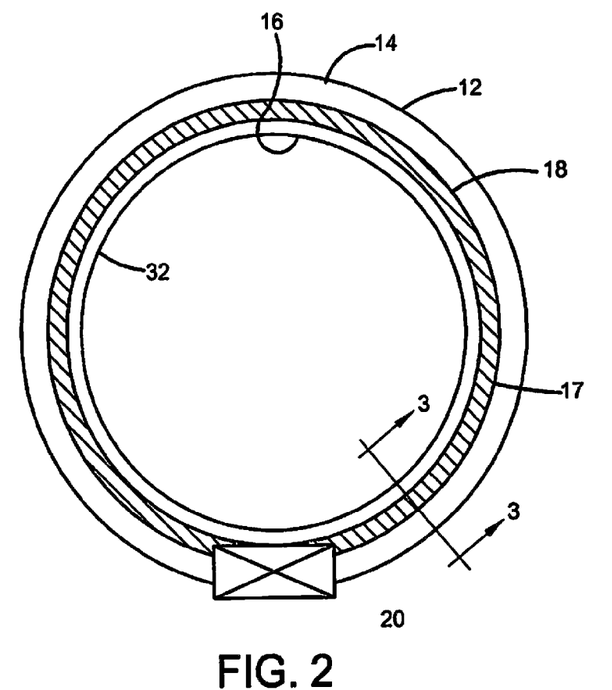
FIG. 2 is a top plan view of the residual limb-prosthesis in accordance with the present invention.
Figure 3A:
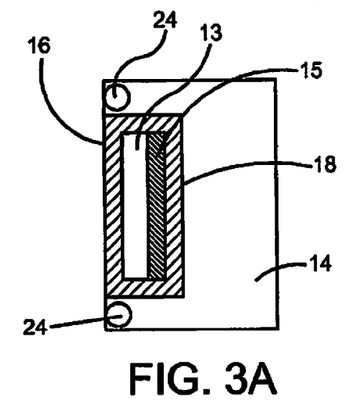
FIG. 3A is a cross-sectional view of a heat pipe of the residual limb-prosthesis taken along the line 3A-3A in FIG. 2.
Figure 3B:
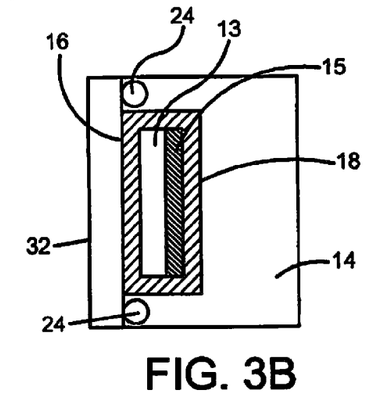
FIG. 3B a cross-sectional view of a heat pipe of the residual limb-prosthesis as in FIG. 3A, but showing an embodiment without a liner.

With reference to FIGS. 1-3, a generic embodiment of a residual limb-prosthesis is shown and designated by the numeral 10. The residual limb-prosthesis 10 includes a socket 12 for receiving a residual limb, wherein the socket 12 includes a socket wall 14 defining a limb-receiving surface 16. The socket 12 can be manufactured from any of the common materials employed for prosthesis sockets in the prior art or hereinafter developed.

At least one heat pipe 18 extends through at least a portion of the socket 12 and includes a working fluid 13 (FIG. 3) and a wicking structure 15. The heat pipe 18 includes a socket section 17 (FIG. 1) and a heat sink section 19, wherein the heat pipe 18 extends along its length through said socket wall 14 proximate to or exposed at the limb-receiving surface 16. In some embodiments, multiple heat pipes may be employed. The heat pipes can extend in the same or different directions and can be placed at various locations, whether horizontally or vertically or at angles therebetween. A single heat pipe could be coil shaped to extend from top to bottom of the socket. This multitude of potential constructions will be evident to those of ordinary skill in the art from the specific concepts taught herein.

In some embodiments, the wicking structure is selected from three common used structures of metal powder, screens and grooved wicks. There are a variety of materials for wicks structures and tubes, as long as they are compatible with working fluid, have a high thermal conductivity and low density. The wick material can be, but not limited to, aluminum, copper, carbon steel, stainless steel, nickel titanium. In some embodiments, the wicking structure is sintered metal powders. The wick and tube materials can be copper or nickel, which are compliable with DI water. In other embodiments, the wicking structure is selected from fabrics.

In some embodiments, the working fluid 13 has a boiling point of from 0° C. or more to 90° C. or less such that the working fluid is adapted to evaporate to form vapor under the influence of the heat of the residual limb in the socket, thus drawing heat from and cooling the residual limb. In some embodiments, the fluid has a boiling point of from 0° C. or more to 50° C. or less, in other embodiments, from 10° C. or more to 40° C. or less, in other embodiments, from 20° C. or more to 36° C. or less, in other embodiments, from 25° C. or more to 36° C. or less, and, in other embodiments, from 28° C. or more to 33° C. or less. In some embodiments, the working fluid 13 is held within the heat pipe 18 under a vacuum such that the boiling point of the working fluid is affected to be different from its value at normal atmospheric conditions. Thus, in some embodiments, any of the above ranges might be met by employing a working fluid under vacuum.

In some embodiments, as seen in FIG. 3A, the limb-receiving surface 16 is the inner surface of the socket wall 14 and the heat pipe 18 is flush with this surface 16. Thus, the heat pipe 18 is exposed at the limb-receiving surface 16 so that it comes in direct contact with the limb in the socket 12. In other embodiments, as seen in FIGS. 1, 2 and 3B, the limb receiving surface 16 is provided by a liner 32 between a limb in the socket 12 and the heat pipe 18. This may be found to be more comfortable for the user. It would also allow for removal and washing of the liner 32.

In some embodiments, the working fluid is selected from water, ethanol, methanol and ammonia and mixtures thereof In some embodiments, the working fluid may be water which is held under a vacuum of 1.23 kPa or less to 3.98 MPa or more to provide a boiling point of 10° C. or less to 36° C. or more. In other embodiments, the working fluid is water held under a vacuum of 1.23 kPa or less to provide a boiling point of from 10° C. or less to 36° C. or more.

In some embodiments, the heat pipe 18 includes a rectangular cross section having a height larger than the width, with the height being the surface area adjacent the limb so as to increase the surface area of contact relative to the volume of the heat pipe. In some embodiments, the heat pipe has a rectangular cross section with a height to width ratio of from 1:1 to 5:1, and the height of the heat pipe 18 is arranged to face a limb in the socket 12 to increase the surface area of the heat pipe 18 facing a limb in the socket 12. It will be readily appreciated that the heat pipe 18 is described as "at least one heat pipe" because multiple heat pipes could be employed at various locations through the socket wall 16, including at the base portion 11 of socket section thereof In other embodiments, the width to height ratio is form 2:1 to 5:1, in other embodiments from 3:1 to 5:1, and in other embodiments from 4:1 to 5:1.

In alternative embodiments, the heat pipe 18 provides a thermal resistance of from 0.16° C./W or more to 0.016° C./W or less. In some embodiments, the heat pipe 18 provides a thermal resistance of 0.16° C./W. In an alternative embodiment, the total thermal resistance is 0.16° C./W±0.02° C./W.

The residual limb-prosthesis 10 further comprises a heat sink 20. The heat sink portion 19 of the heat pipe 18 passes through the heat sink 20. The heat sink 20 reduces the temperature of the working fluid to condense the vapor within the heat pipe 18 back to the working fluid. The wicking structure 15 within the heat pipe 18 collects the working fluid 13 and draws it back to the socket 12 through capillary action. The heat sink 20 may be any suitable device for drawing heat from the heat pipe 18 in order to reduce the temperature to condense vapor. In some embodiments, the heat sink 20 could be fan-based or cooling package based.

The residual limb-prosthesis 10 further comprises a control system 22 for controlling the operation of the heat sink 20. The control system 22 includes a heat sensor 24 which monitors the temperature at the interface between the residual limb and the socket 12, and communicates with a regulator 26 to regulate the effectiveness of the heat sink 20. The regulator 26 regulates the effectiveness of the heat sink 20 by processing a signal 27 (represented by dash lines in FIG. 1) from one or more heat sensors 24. In some embodiments the control system 22 includes a processor 28 to receive the signal 27 from the heat sensor 24 and output an appropriate control to the heat sink 20, as represented at dashed line 35, to increase or decrease heat transfer from the heat pipe 18 to the heat sink 20. The processor 28 receives the signal 27 from the heat sensor 24 and automatically adjusts the regulator 26 to regulate the temperature at the socket 14 surface. In some embodiments, the control system 22 includes a manual control 25 which communicates with a signal 29 which further communicates with the heat sink 20 to regulate the effectiveness of the heat sink 20, thereby adjusting the temperature at the socket 12 surface at the control of the amputee.

It will be appreciated that, just as with the heat pipe 18, a plurality of heat sensors 24 can be employed. In some embodiments, a mean temperature is calculated from multiple heat sensors and employed in the control. In some embodiments, the heat sensor(s) and regulator maintain the residual limb at a temperature between 20-32° C. In some embodiments, the heat sensor(s) and regulator maintain skin temperature at 31.4° C. at various thermal loads of said residual limb. In some embodiments, the heat sensors are thermistors.

Figure 4A:
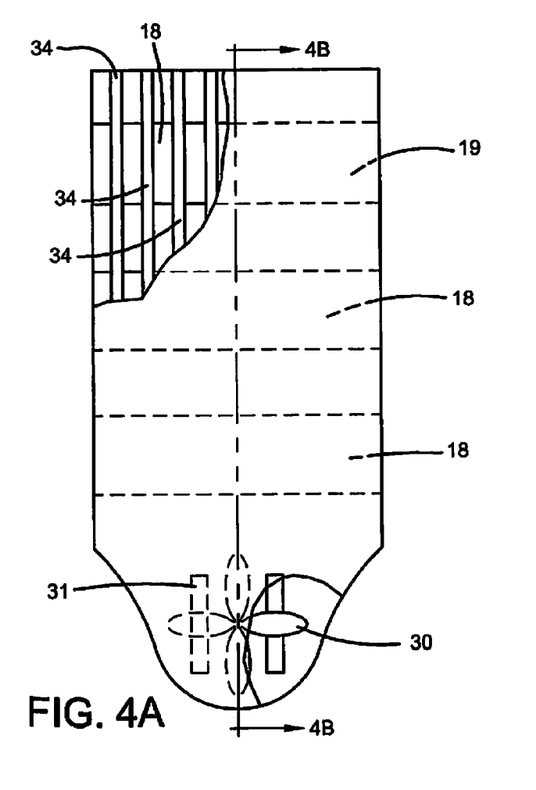
FIG. 4A is a rear plan view of a fan-based heat sink in accordance with the present invention.
Figure 4B:
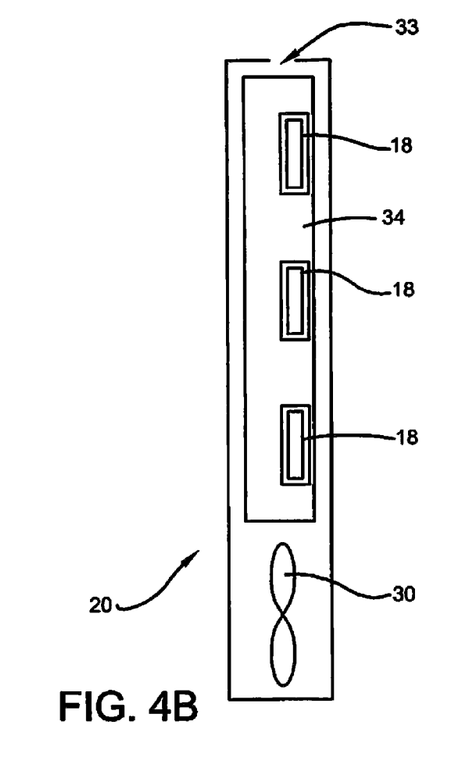
FIG. 4B is a cross-sectional view of the fan-based heat sink taken along the line 4B-4B in FIG. 4A.
Figure 4C:
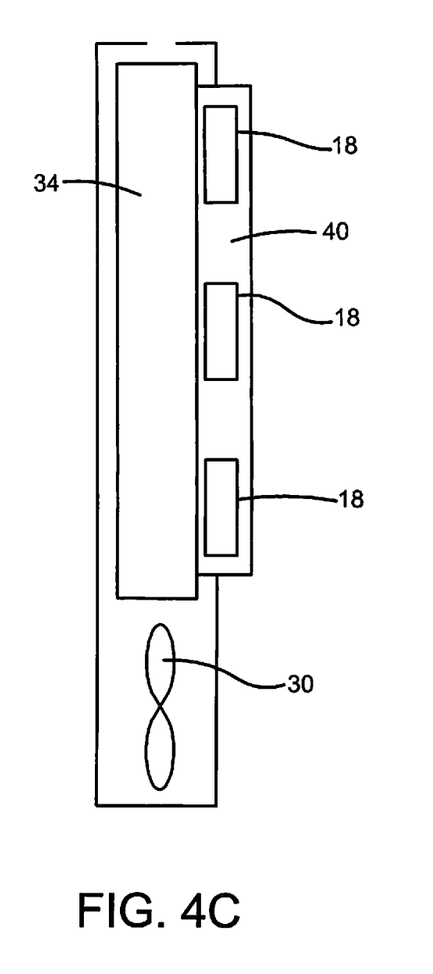
FIG. 4C is a cross-sectional view of a fan-based heat sink as in FIG. 4B, but showing an alternative embodiment employing a heat collector structure.

Referring now to FIGS. 4A, 4B and 4C, in some embodiments, the heat sink 20 is fan-based. The heat sink 20 includes a fan 30 operable to blow air across a heat pipe 18. In some embodiments, to improve the heat transfer, the heat sink 20 includes a plurality of fins 34 that are in direct contact with the heat pipe 18. In FIG. 4B, the heat pipe(s) 18 extend through the fins 34, but in other embodiments, the heat pipe(s) can be adjacent to and abuttingly engage the plurality of fins 34. In FIG. 4C, the heat pipe(s) 18 run through a heat collector structure 40 that is in contact with the fins 34. The heat collector structure would have a high thermal conductivity to transfer heat to the fins 34. The heat collector structure is typically metal. The fan 30 is positioned to be operable to blow air across the plurality of fins 34, drawing air in at inlet 31 and expelling air at outlet 33. In such embodiments, a fan 30 can be powered by a battery. In some embodiments, the battery can be a Lithium-ion battery or the like.

Figure 5:
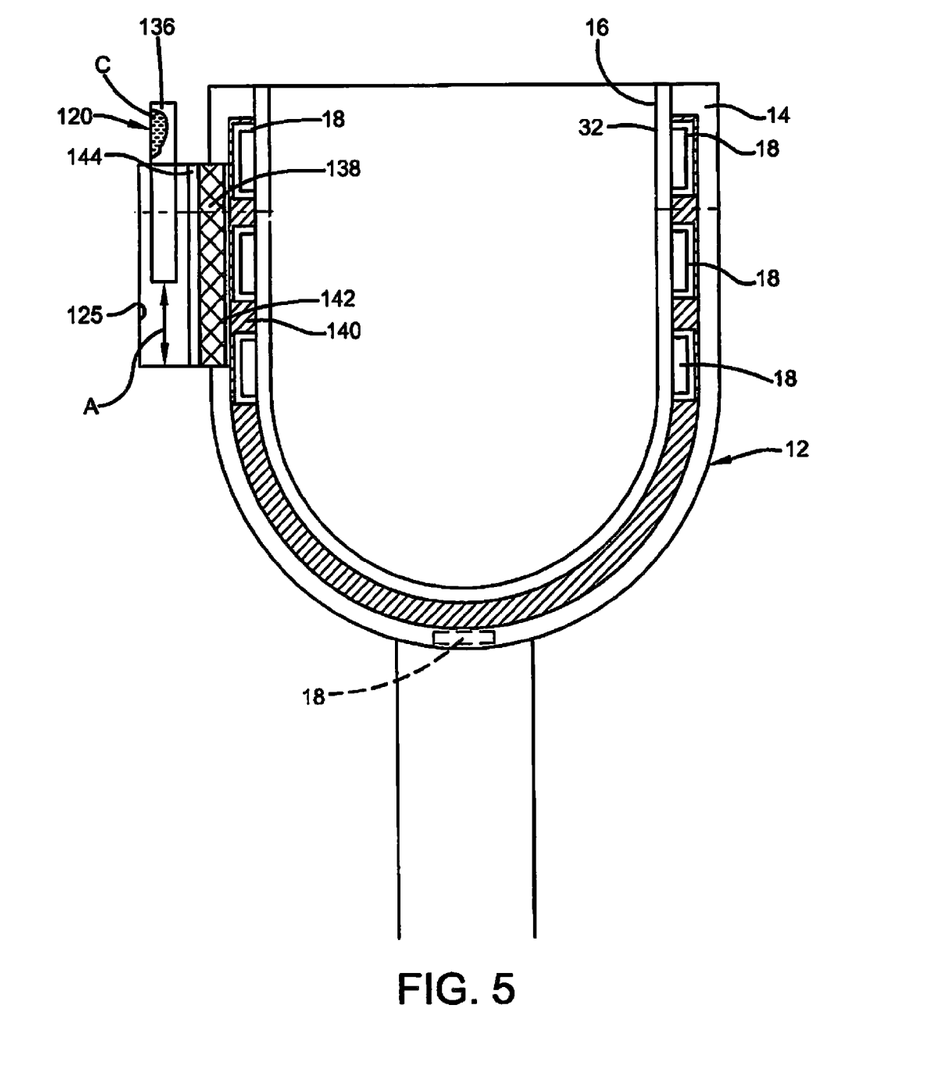
FIG. 5 is a side elevational view of the residual limb-prosthesis in accordance with the present invention, shown with a cooling package based heat sink.
Figure 6:
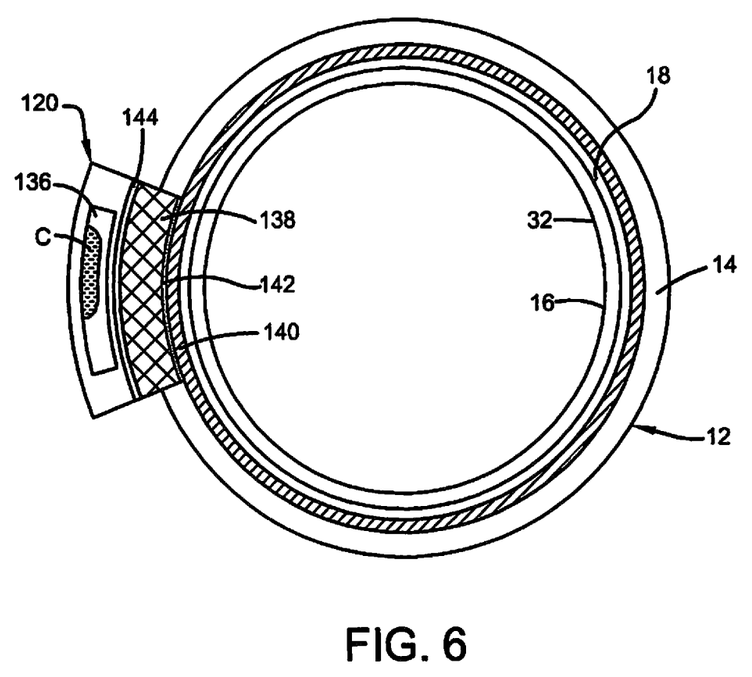
FIG. 6 is a cross-sectional view taken along the line 6-6 in FIG. 5.

Referring now to FIGS. 5 and 6, in alternative embodiments, a heat sink 120 is cooling package based. The figure will generally be appreciated as showing many features of the general embodiment of FIG. 1, but with a different heat sink. The heat sink 120 includes a cooling package 136 that is filled with a cold source material C. The cold source material has a temperature less than that of the vapor formed in the heat pipe 18. In some embodiments, the cold source material has high latent heat, high thermal conductivity and a working temperature range compactable with the cooling system. In some embodiments, cold source material is selected from ice, dry ice and refrigerant gel. The cooling package 136 is received by a receptacle 125 of the heat sink 120 and can be inserted and removed therefrom, as represented at arrow A. The cooling package 136 can therefore be removed and frozen as needed, as its temperature slowly comes to ambient temperature during use.

It may be found that the phase change materials provide too high a heat removal rate, causing discomfort to the prosthesis wearer. Thus, in some embodiments, the heat sink 120 includes a variable insulator 138 that is positioned between the cooling package 136 and the heat pipe 18, the variable insulator 138 being operable to vary the amount of heat transfer between the heat pipe 18 and the cooling package 136. In some embodiments, the heat sink 120 further includes a heat collector structure 140 that communicates between the heat pipe 18 and the variable insulator 138. The variable insulator 138 further includes a heat transfer plate 142 which communicates with the heat collector structure 140. In other embodiments, the heat collector structure is not employed, and the heat transfer plate 142 communicates directly with the one or more heat pipes 18 employed. Optionally, the variable insulator 138 includes a second heat transfer plate 144 communicating with the cooling package 136.

Figure 7:
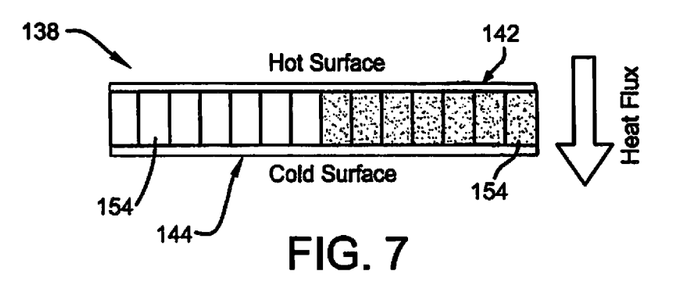
FIG. 7 is a cross-sectional view of a variable insulator of a cooling package based heat sink in accordance with the present invention.
Figure 8:
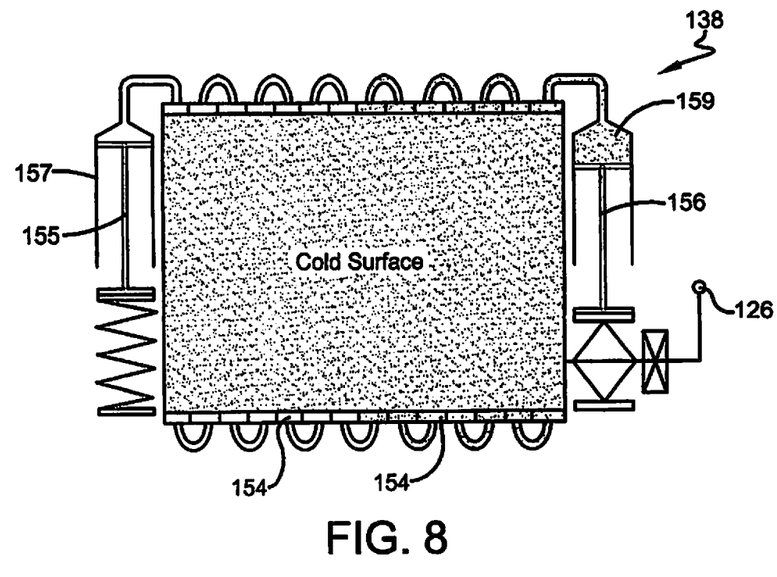
FIG. 8 is a top plan view of the variable insulator of FIG. 7.

Referring now to FIGS. 7 and 8, in alternative embodiments, the variable insulator 138 includes a plurality of chambers 154 that communicated between said heat transfer plate 142 and a second heat transfer plate 144, where the plurality of chambers 154 is adapted to hold air or coolant based on the operation of and an air piston 155 in an air chamber 157 and a coolant piston 156 in a coolant chamber 159. The insulation offered by said variable insulator 138 is varied by adjustment of the amount of air and coolant in said plurality of chambers 154. The amount of air and coolant in the chambers 154 is varied by the positioning of the pistons, forcing more air or more coolant into the chambers 154. The air will provide more insulation, when the interface is too cool, and coolant will provide less insulation, when the interface it too hot. The amount of air and coolant will be adjusted by a regulator, such as regulator 126, which, instead of controlling a fan, will control the air and coolant pistons 155 and 156, respectively. The output of the regulator 126 would be based on feedback of temperature measured by the one or more heat sensors.

Figure 9:
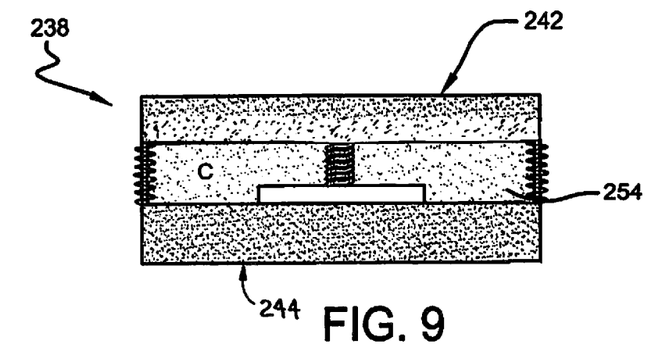
FIG. 9 is a side elevational view of an alternative variable insulator.

With reference to FIG. 9, in some embodiments, a variable insulator 238 is employed between a heat transfer plate 242 and a second heat transfer plate 244. The heat transfer plate 242 communicates either directly with the one or more heat pipes 18 or with a heat collector structure 140, as shown in FIG. 5. The variable insulator 238 includes a coolant chamber 254 holding coolant C and communicating between the heat transfer plate 242 and the second heat transfer plate 244, the volume of the coolant C in the coolant chamber 254 being variable such that the insulation offered by said variable insulator 238 is varied by adjustment of the volume of the coolant chamber 254, which adjustment also adjusts the effective surface area of contact between the coolant package and the heat transfer plate 242. Chambers, not shown, could be employed to take up coolant expelled from coolant chamber 254. The thermal resistance is adjusted by adjusting the volume and/or surface area of contact between the coolant C and the heat transfer plate 242, thus adjusting the effectiveness for the cooling package.

Figure 10:
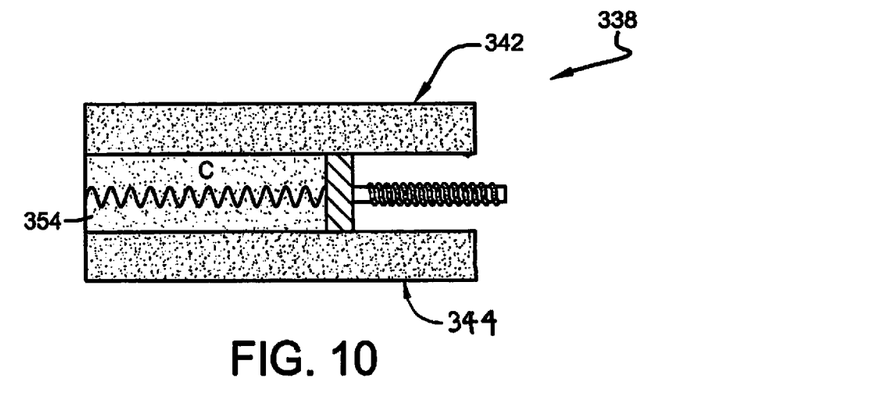
FIG. 10 is a side elevational view of another alternative variable insulator.

With reference to FIG. 10, in some embodiments, a variable insulator 338 is employed between a heat transfer plate 342 and a second heat transfer plate 344. The heat transfer plate 342 communicates either directly with one or more heat pipes 18 or with a heat collector structure 140, as shown in FIG. 5. The variable insulator 338 includes a coolant chamber 354 holding coolant C and communicating between the heat transfer plate 342 and the second heat transfer plate 344, the volume of the coolant C in the coolant chamber 354 being variable such that the insulation offered by said variable insulator 338 is varied by adjustment of the volume of the coolant chamber 354, which adjustment also adjusts the effective surface area of contact between the coolant package and the heat transfer plate 342. Chambers, not shown, could be employed to take up coolant expelled from coolant chamber 354. The thermal resistance is adjusted by adjusting the volume and/or surface area of contact between the coolant C and the heat transfer plate 342, thus adjusting the effectiveness for the cooling package.

Figure 11:
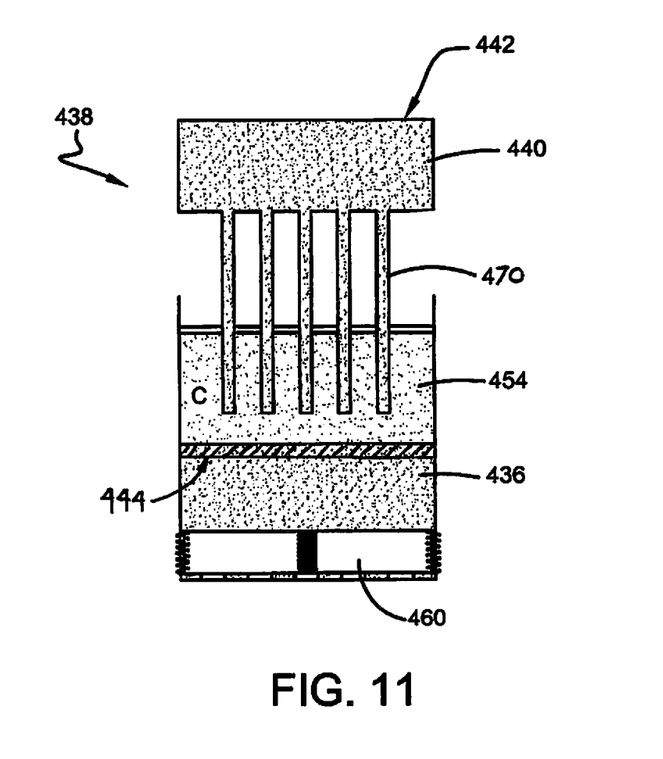
FIG. 11 is a side elevational view of yet another alternative variable insulator.

Referring now to FIG. 11, in other embodiments, a variable insulator 438 is employed between a heat transfer plate 442 and a second heat transfer plate 444 the thermal resistance includes a set of high efficiency heat transfer tubes 470 and a chamber 454 holding coolant C, wherein the surface area of contact between said heat transfer tubes and said coolant C is variable such that the insulation offered by said variable insulator 438 is varied by adjustment of the surface area of contact between said heat transfer tubes 470 and said coolant C. The heat transfer plate 442 communicates either directly with one or more heat pipes or with a heat collector structure. When the heat transfer tubes 470 are immersed in coolant C, the immerse depth of the heat transfer tubes 470 can be controlled by a screw 460 positioned to press a cooling package 436, plate 444 and chamber 254 toward the heat transfer tubes 470 to alter the contact area and total effective thermal resistance.

In light of the foregoing, it should be appreciated that the present invention significantly advances the art by providing a residual limb-prosthesis that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A residual limb-prosthesis comprising:
a socket for receiving a residual limb, said socket having a socket wall defining a limb-receiving surface;
a heat pipe including a working fluid and a wicking structure, said heat pipe having a socket section and a heat sink section, said heat pipe extending along its length through said socket wall proximate to or exposed at said limb-receiving surface, wherein said working fluid has a boiling point of from 0° C. or more to 90° C. or less at normal atmospheric conditions such that said working fluid is adapted to evaporate to form vapor under the influence of the heat of a residual limb in the socket thus drawing heat from and cooling the residual limb;
a heat sink, said heat sink section of said heat pipe passing through said heat sink, said heat sink reducing the temperature of the working fluid so as to condense vapor within said heat pipe back to working fluid, said wicking structure collecting said working fluid and drawing it back to said socket section, wherein said heat pipe has a rectangular cross-section relative to said length of said heat pipe the rectangular cross section having height and width, with the height larger than the width, with the height being the surface area adjacent the limb so as to increase the surface area of contact relative to the volume of the heat pipe.

2. A residual limb-prosthesis comprising:
a socket for receiving a residual limb, said socket having a socket wall defining a limb-receiving surface;
a heat pipe including a working fluid and a wicking structure, said heat pipe having a socket section and a heat sink section, said heat pipe extending along its length through said socket wall proximate to or exposed at said limb-receiving surface, wherein said working fluid has a boiling point of from 0° C. or more to 90° C. or less at normal atmospheric conditions such that said working fluid is adapted to evaporate to form vapor under the influence of the heat of a residual limb in the socket thus drawing heat from and cooling the residual limb;
a heat sink, said heat sink section of said heat pipe passing through said heat sink, said heat sink reducing the temperature of the working fluid so as to condense vapor within said heat pipe back to working fluid, said wicking structure collecting said working fluid and drawing it back to said socket section, wherein said heat sink includes a cooling package filled with a cold source material having a temperature less than that of the vapor formed in said heat pipe.

3. The prosthesis of claim 2, wherein said cold source material is selected from ice, dry ice, and refrigerant gel.

4. The prosthesis of claim 3, wherein said heat sink includes a variable insulator positioned between said cooling package and said heat pipe and operable to vary the amount of heat transfer between said heat pipe and said cooling package.

5. The prosthesis of claim 4, further comprising a heat collector structure communicating between said heat pipe and said variable insulator.

* * * * *